United States Patent
Einspanier

(10) Patent No.: US 11,596,130 B2
(45) Date of Patent: Mar. 7, 2023

(54) EGG INSPECTION DEVICE

(71) Applicant: SELEGGT GMBH, Cologne (DE)

(72) Inventor: Almuth Einspanier, Leipzig (DE)

(73) Assignee: SELEGGT GMBH, Cologne (DE)

( * ) Notice: Subject to any disclaimer, the term of this patent is extended or adjusted under 35 U.S.C. 154(b) by 243 days.

(21) Appl. No.: 16/997,675

(22) Filed: Aug. 19, 2020

(65) Prior Publication Data

US 2020/0375153 A1 Dec. 3, 2020

Related U.S. Application Data

(63) Continuation of application No. 16/324,838, filed as application No. PCT/EP2017/069769 on Aug. 4, 2017.

(30) Foreign Application Priority Data

Aug. 12, 2016 (DE) ...................... 10 2016 215 127.4

(51) Int. Cl.
*A01K 43/00* (2006.01)
*A01K 45/00* (2006.01)
(Continued)

(52) U.S. Cl.
CPC ............ *A01K 43/00* (2013.01); *A01K 45/007* (2013.01); *B65G 47/90* (2013.01); *G01N 1/14* (2013.01);
(Continued)

(58) Field of Classification Search
CPC ........ A01K 43/00; A01K 45/007; G01N 1/14; G01N 33/08; B65G 47/90; B65G 2201/0208
(Continued)

(56) References Cited

U.S. PATENT DOCUMENTS

| 1,472,674 A | 10/1923 | Reagan |
| 5,460,083 A | 10/1995 | Hutchinson et al. |
| 5,784,992 A | 7/1998 | Petitte et al. |

(Continued)

FOREIGN PATENT DOCUMENTS

| CA | 2440659 C | 10/2008 |
| CN | 1313726 A | 9/2001 |

(Continued)

OTHER PUBLICATIONS

Li, S., "Research on the key technology of online intelligent detection of poultry egg quality—Study on the Key Technologies for Egg Quality Intelligent and On-Line Detection System," Ph.D. in Processing and Storage of Agriculture Products Dissertation, Jiangsu University, Jun. 2013, Available Online Aug. 15, 2013, 134 pages. (Submitted with English Abstract).

(Continued)

*Primary Examiner* — James R Bidwell
(74) *Attorney, Agent, or Firm* — McCoy Russell LLP

(57) ABSTRACT

An egg-examining device, comprising a sampling device, by which a liquid sample to be taken can be taken from an egg of a rack loaded with eggs, a feeding device for feeding the rack loaded with eggs to the sampling device, and a control unit, by which the feeding device and the sampling device can be controlled. The feeding device feeds the rack to the sampling device at an oblique angle of between 20° and 80° to a plane perpendicular to the direction of gravity. A lifting-out device is provided, by which the egg can be lifted out of the rack and by which the egg can be put into a sampling position, in which the liquid amount to be taken can be taken from the egg by the sampling device.

11 Claims, 8 Drawing Sheets

(51) Int. Cl.
*G01N 33/08* (2006.01)
*G01N 1/14* (2006.01)
*B65G 47/90* (2006.01)

(52) U.S. Cl.
CPC ..... *G01N 33/08* (2013.01); *B65G 2201/0208* (2013.01)

(58) Field of Classification Search
USPC .......................................................... 356/52
See application file for complete search history.

(56) References Cited

U.S. PATENT DOCUMENTS

| | | | |
|---|---|---|---|
| 5,898,488 A | 4/1999 | Kuhl | |
| 6,176,199 B1 * | 1/2001 | Gore | A01K 41/065 119/6.8 |
| 6,244,214 B1 | 6/2001 | Hebrank | |
| 8,245,632 B1 | 8/2012 | Fields | |
| 8,400,621 B2 | 3/2013 | Nadreau et al. | |
| 9,686,969 B2 * | 6/2017 | Meissner | A01K 43/04 |
| 10,060,854 B2 * | 8/2018 | Schortgen | G01N 33/085 |
| 2002/0150460 A1 | 10/2002 | Chalker, II et al. | |
| 2002/0169411 A1 | 11/2002 | Sherman et al. | |
| 2009/0201323 A1 | 8/2009 | Robert et al. | |
| 2013/0008475 A1 | 1/2013 | Robinson | |
| 2015/0337372 A1 | 11/2015 | Winger et al. | |
| 2016/0030240 A1 | 2/2016 | Gonenc et al. | |

FOREIGN PATENT DOCUMENTS

| | | |
|---|---|---|
| CN | 101123876 A | 2/2008 |
| CN | 101283087 A | 10/2008 |
| CN | 101409034 A | 4/2009 |
| CN | 102239812 A | 11/2011 |
| CN | 203194488 U | 9/2013 |
| CN | 203542821 U | 4/2014 |
| CN | 204638316 U | 9/2015 |
| DE | 69918321 T2 | 8/2005 |
| DE | 102015226490 A1 | 6/2017 |
| EP | 2159564 A2 | 3/2010 |
| EP | 2505217 A2 | 10/2012 |
| EP | 1379123 B1 | 2/2013 |
| EP | 2786656 A1 | 10/2014 |
| RU | 2161404 C1 | 1/2001 |
| RU | 244978 C2 | 2/2012 |
| RU | 2013122392 A | 12/2014 |
| RU | 2583687 C2 | 5/2016 |
| WO | 8500621 A1 | 2/1983 |
| WO | 9314629 A1 | 8/1993 |
| WO | 2016015607 A1 | 2/2016 |

OTHER PUBLICATIONS

Diansheng, H., "Reverse Design and Prototype Test of Chain Egg Beater," Master's of General Service Industry Thesis, Huazhong Agricultural University, Feb. 15, 2016, 72 pages.

ISA European Patent Office, International Search Report Issued in Application No. PCT/EP2017/069769, dated Sep. 13, 2017, WIPO, 4 pages.

Russian Federal Institute of Industrial Property, Office Action Issued in Application No. 2019103924/04(007337), dated Dec. 26, 2019, 7 pages.

* cited by examiner

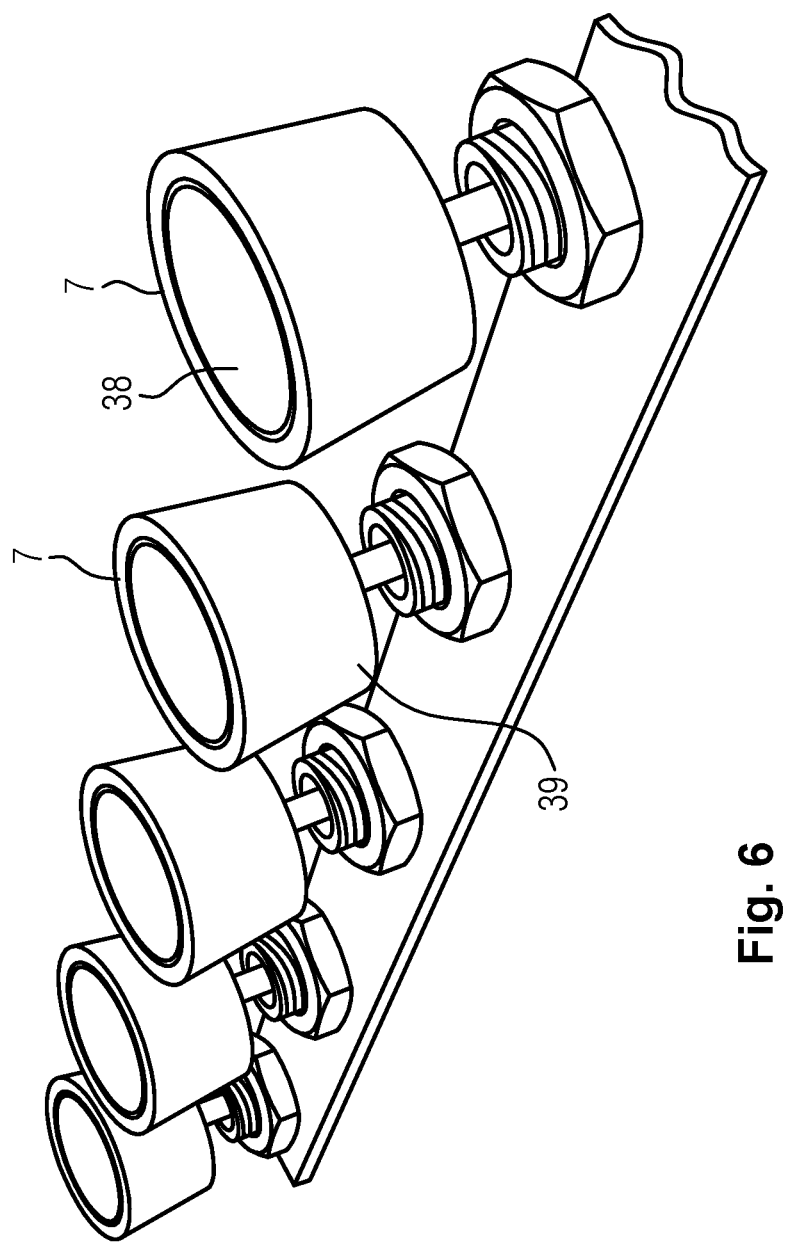

EGG INSPECTION DEVICE

CROSS-REFERENCE TO RELATED APPLICATIONS

The present application is a continuation of U.S. patent application Ser. No. 16/324,838, entitled "EGG INSPECTION DEVICE," filed on Feb. 11, 2019. U.S. patent application Ser. No. 16/324,838 is the U.S. National Phase of International Patent Application Serial No. PCT/EP2017/069769, filed on Aug. 4, 2017. International Patent Application Serial No. PCT/EP2017/069769 claims priority to German Patent Application No. 10 2016 215 127.4 filed on Aug. 12, 2016. The entire contents of each of the above-referenced applications are hereby incorporated by reference for all purposes.

TECHNICAL FIELD

The present invention relates to an egg inspection device, in particular to an egg sex determination device. A generic egg inspection device is known for example from EP 2 786 656 A1.

BACKGROUND AND SUMMARY

In the device described in EP 2 786 656 A1, liquid samples are taken from an array of eggs by means of cannulas in order to be able to characterize the eggs more precisely on the basis of the characteristic properties of the respective liquid sample.

For example, a predetermined amount of allantoic liquid is taken from the eggs to determine the sex of embryonic chicks.

A plurality of eggs is accommodated in a grid-like array into a rack. In said rack, the eggs lie in their horizontal direction, i.e. the axis of rotation of the egg is perpendicular to the direction of gravity. Since the eggs are not arranged in a non-rotating manner in the rack, the eggs in the device according to EP 2 786 656 A1 are fixed and positioned in their horizontal direction within the rack by means of a forming punch which is pressed laterally onto the egg.

The shell is then punctured using a thin cannula provided on a sampling device which pierces the egg from the side, i.e. perpendicular to the horizontal direction of the egg, to extract a liquid sample.

The method described in this prior art is relatively inaccurate, because a positioning of the eggs and thus an extraction of a liquid at a specific location within the egg is not always guaranteed.

Based on the foregoing, the invention proposes an egg inspection device in order to solve the above problem.

This is characterized in that the feeding system is arranged to feed the rack to the sampling device at an oblique angle of between 20° and 80° to a plane perpendicular to the direction of gravity, and an excavating device is provided, by means of which the egg can be lifted out of the rack and by means of which the egg can be brought into a sampling position in which the quantity of liquid to be removed can be extracted from the egg by means of the sampling device, wherein the lifting-out device is controllable by means of the control unit.

Particularly when allantoic liquid is extracted, it has been shown that if the eggs are not pierced perpendicularly to the horizontal but slightly obliquely to the axis of rotation, preferably obliquely from the rear of the egg, an area within the egg is hit in order to be able to extract predetermined amounts of liquid in a reproducible manner. If the egg is twisted by the previously described angle with respect to its base, the allantoic liquid accumulates to a suitable extent at a well-defined point in the egg so that a desired amount of allantoic liquid can be extracted through the cannula. Particularly preferred angle ranges are between 30° and 60°, preferably 40° to 50°, in particular 45°. The corresponding angle ranges may each form upper or lower limits of the egg alignment. In addition, it has been shown that a good puncture force is guaranteed under the angle ranges described above, without permanent damage to the shell leading to breakage of the egg. Since the eggs lie either horizontally or vertically in the rack, in particular vertically, i.e. the longitudinal axis of the eggs is perpendicular to the rack plane, there is a corresponding oblique angle at which the individual eggs are transferred from the lifting-out device to the sampling device. From the lifting-out device, the eggs are preferably brought out perpendicularly to the rack or the surface formed by the rack or perpendicular to the inclined feeding plane, preferably through the dimensions of the rack, and fixed in this position, e.g. by a corresponding device. After such an egg has been sampled, i.e. a corresponding amount of liquid has been taken from it, it can be returned to the rack with the lifting-out device and the rack is preferably moved translationally in the same oblique angle in order to sample the next egg in the rack. In this way, essentially all eggs arranged diagonally one behind the other in the inclined rack can be sampled one after the other. For sampling, the respective egg is lifted out of the rack by means of a lifting-out device and positioned in the sampling position. Since the racks are already fed obliquely, the eggs can be pierced obliquely while they are individually lifted.

According to a further aspect of the invention, the lifting-out device can be configured such that it can rotate an egg lifted with the lifting-out device into a predetermined puncture position. When the egg is lifted out of the rack by the lifting-out device, it may occur that it is not in a position where the sampling would ideally take place. Often the egg can be rotated by rotation, e.g. around its longitudinal and/or transverse axis, to be brought into a better sampling position. This can be achieved by vibrating, for example, or by electrically driven rollers on the lifting-out device.

According to a further aspect of the invention, the lifting-out device may be a mechanical lifting-out device, or an air-stream operated lifting-out device in which the egg is lifted by means of an air-stream. As far as a mechanical lifting-out device is concerned, a design as described below with an egg stamp and a stop element is advantageous. However, the egg can also be lifted out by means of an air stream and pressed against a stop element, for example, in order to be brought into the correct position. In this case, a hose with an opening below the egg is positioned in the rack and the egg is lifted in the air stream using compressed air.

In order to enable the positioning and alignment of the egg to be sampled, a guided lifting of the egg is advantageous that may be done via the egg stamp, preferably via a rotatably mounted egg stamp and/or via an air stream. The egg is then held in position from the other side, e.g. with a soft suction cup. This fixation can also be done mechanically and/or by air stream. In addition, the egg can be guided ventrally into position.

According to a further aspect of the invention, the sampling device may have a cannula connected to a vacuum generating device, the quantity of liquid to be extracted from the egg being controllable by means of the control unit via the pressure generated in the vacuum generating device. The control unit may control a pneumatic system formed, for example, by a vacuum hose connected to the cannula and connected to a vacuum generator. By controlling the pressure, a well-defined amount of liquid can be extracted from the egg after the cannula has obliquely pierced the egg shell. With such a pneumatic system and sampling via vacuum control, mechanical elements similar to those present when simple piston syringes are used as sampling devices can be reduced. The sampling device with the cannula protruding from it can be moved vertically, i.e. in the direction of gravity, for sampling, with the cannula or tip of the cannula piercing the egg shell and taking the corresponding predetermined amount of liquid, e.g. from the allantois. Preferred cannula outer diameters are 0.55 mm; 0.60 mm; 0.65 mm; 0.70 mm; 0.75 mm; 0.80 mm and preferred cannula inner diameters are 0.10 mm; 0.15 mm; 0.20 mm, 0.25 mm, 0.30 mm; 0.35 mm; 0.40 mm; 0.45 mm; 0.50 mm. The above values can each be upper or lower limits of a cannula thickness range.

According to a further aspect of the invention, the sampling device may have a cannula revolver with several cannulas. A cannula revolver may be provided as a rotatable device in which the cannula is rotated after each puncture, preferably by means of the control unit. Thus, a new or different cannula can be used for each puncture. This ensures faster process control. Preferably, while the other cannula is used for piercing, the cannula with which the egg was previously pierced can be cleaned at the same time. Combining piercing and cleaning the needle in one step can save time in sampling and cleaning. The cannula revolver can have several needles, in particular 6 needles.

According to a further aspect of the invention, the cannula may include at least two openings through which the amount of liquid to be extracted can be taken from the egg. It has been shown that sometimes, because the position of membranes within the egg is not the same even when the egg is always oriented in the same way, if only a single opening is provided at the tip of the cannula, problems may occur with liquid extraction because such a membrane covers the opening. If at least two openings are provided, in particular exactly two openings, it is unlikely that both openings will be covered at the same time.

According to a further aspect of the invention, the cannula may include at least two openings by means of which the amount of liquid to be extracted can be taken from the egg. It has been shown that sometimes, because the position of membranes within the egg is not the same even when the egg is always aligned in the same way, provided that only a single opening is intended at the tip of the cannula, problems may arise during liquid extraction because such a membrane covers the opening. If at least two openings are provided, in particular exactly two openings, it is unlikely that both openings will be covered at the same time.

According to a further aspect of the invention, a protruding length of the cannula, with which this protrudes from the contact surface provided on the sampling device, which comes into contact with the egg during sampling, may be adjustable. Since the eggs arranged in a rack can be of different sizes, e.g. depending on the laying age of the hen or the genetics, a different puncture depth of the cannula may be necessary depending on the egg size in order to extract the amount of liquid from the egg. The optimum puncture depth can be determined automatically by imaging methods. The protruding length of the cannula is preferably adjusted automatically for each egg.

After a definite sampling situation has been found, the sampling device is always pressed vertically on the egg until the cannula has completely disappeared into the egg. The immersion of the needle in liquid/allantois can be confirmed via a control device and the defined suction process can be started.

For example, it may also be detected as soon as the egg hits a contact surface of the sampling device. As soon as this contact surface is touched by the egg, which can be measured by means of optical methods such as a camera or a pressure sensor on the contact surface, the control unit instructs the sampling device to stop its movement. The length of the cannula protruding from the sampling device therefore determines the depth at which the liquid is extracted from the egg. According to a further aspect of the invention, the protruding length of the cannula can be adjusted by means of the control unit. For example, the control unit can adjust and vary the length of the cannula depending on the information about the egg, and thus selectively predetermine a depth for each corresponding egg depending on its properties, e.g. its thickness, from which the amount of liquid is taken.

Alternatively or additionally, or also if the protruding cannula length cannot be changed, the control unit can move the sampling device forward until the cannula is immersed in the liquid in the egg (allantois). The control unit may, for example, detect the cannula being immersed in a liquid (allantois) and stop the forward movement of the sampling unit when the desired depth is reached. The suction process is then started, for example.

According to a further aspect of the invention, the sampling device can identify a light barrier which can be used by means of the control unit to determine whether the amount of liquid extracted from the egg corresponds to the amount of liquid to be extracted and cannot be altered by air bubbles. The light barrier can be provided in a position in which, for example, the vacuum hose or another transparent element through which the liquid is sucked in is illuminated. As soon as so much liquid has been drawn in via the cannula that the predetermined amount of liquid has been reached, the light barrier can determine the meniscus and thus the amount of liquid extracted from the egg. Preferred amounts of liquid may be 1 µl to 50 µl, preferably 5 to 30 µl, in particular 10 to 20 µl. The above values may form upper and lower limits. Particularly when extracting such small amounts of liquid, the determination of the extracted amount of liquid using light barriers has proven to be a good solution in order to carry out an exact determination of the extraction amount and, if necessary, to detect air bubbles.

Several light barriers may also be provided, e.g. light barriers based on different colored light. For example, problems that occur when measuring the amount of liquid taken can be minimized, in the event that red blood cells are present in the extracted liquid.

According to a further aspect of the invention, at least two sampling devices may be provided which are combined in one sampling unit so that each sampling device of the at least two liquid samples to be taken at the same time may be used to extract the liquid sample from one egg of each rack, and at least two lifting-out devices may be provided, wherein by means of the respective lifting-out device of the at least two lifting-out devices, the egg of the rack associated with the respective sampling unit may be lifted out of the rack and brought into the sampling position. In particular, more than two sampling devices are provided.

According to this further aspect, at least two sampling devices may be provided, each of which is associated with a lifting-out device, whereby each lifting-out device lifts an egg from the rack and feeds it to the respective sampling device. In this way, at least two eggs may be sampled simultaneously. This further aspect may also include more than two sampling devices and correspondingly, more than two lifting-out devices so that, for example, three, four, five or even ten eggs may always be sampled simultaneously. The corresponding eggs of the racks which can be sampled at the same time, should preferably be placed next to each other in a row of the rack in a transverse direction to the inclination of the rack.

For example, it is possible that at least two or more eggs can always be sampled side by side using a plurality of corresponding sampling devices and, after the corresponding row of eggs has been sampled, the rack will be moved by one unit to sample the row of eggs lying below in the oblique direction.

Insofar as the rack comprises more eggs next to each other (transverse to the inclined position) than sampling devices are provided for, the sampling unit with the sampling devices can also be moved in this horizontal direction, thus, in the direction of the eggs lying next to each other in a row, by means of the control unit. For example, two, three, four or five eggs lying next to each other in a row can be sampled simultaneously. After sampling an entire row of eggs from a rack in the horizontal direction, the next row below in the oblique direction is sampled.

The configuration of at least two sampling devices with one lifting-out device directed to this device provides a fast procedure so that several eggs can always be sampled at the same time.

According to a further aspect, the control unit can be configured in such a way that for each of the at least two sampling devices it individually adjusts the amount of liquid to be taken from the egg depending on the egg parameters of the egg assigned to the sampling device.

Depending for example on the egg size or the hatching day of the egg, the amount of allantoic liquid contained in the egg may vary. It is therefore convenient to set the amount of allantoic liquid to be extracted individually for each of the at least two or more sampling devices, depending on previously determined egg parameters. For this purpose, it may be provided that the pressure in the corresponding vacuum hoses assigned to each sampling device can be individually adjusted to extract an appropriate amount of liquid. The positioning of the preferably provided light barriers for determining the quantity of liquid extracted can therefore also be controlled by the control unit depending on the amount of liquid to be extracted.

According to a further aspect of the invention, the sampling device may be movable in the direction of gravity. In addition, the sampling device may be movable parallel to the surface within which the rack is translationally movable by the feeding device, and transverse to the direction of translation of the rack prescribed by the feeding device.

In particular, the sampling device moves in the direction of gravity and in the direction of the individual eggs in rows side by side transversely to the direction of translation of the rack, that is parallel to the surface within which the rack can be translationally moved by the feeding device, and in the direction transversely to the direction of translation of the rack prescribed by the feeding device. For example, the control unit can control an actuator that interacts with the sampling device. This means that the sampling device can be moved in at least two directions within one plane. Such translational operability can be provided both for the case of a single sampling device and for the case where several sampling devices are combined in one sampling unit. If all sampling devices are combined in the sampling unit, it is possible to move all sampling devices simultaneously in a uniform manner. The direction of movement in the direction of gravity is intended to move the sampling device towards the respective egg, for example to press the cannula into the egg shell. The movement in translation direction is intended, for example, for the sampling of eggs lying in rows next to each other transversely to the feeding device in the rack. If all eggs lying next to each other in the rack are sampled simultaneously with the sampling devices combined in one sampling unit, such movement in translational direction can be omitted completely.

According to a further aspect of the invention, a sample collection device can be provided which takes up the amount of liquid extracted from the egg by the sampling device. Such a sample collection device can be any vessel or nonwoven assigned to the egg inspection device into which the amount of liquid extracted from the egg by the sampling device can be delivered. It is a matter of course that preferably the liquid extracted from an egg is placed in a corresponding empty sample collection device, e.g. the empty vessel or an unused nonwoven, and therefore as many sample collection devices can be provided as eggs are contained in the rack.

According to a further aspect of the invention, at least two sample collection devices combined in one unit may be provided from which the respective amount of liquid extracted from the respective egg by the at least two sample collection devices can be delivered. As soon as, for example, two or more sampling devices are provided next to each other, it is also advantageous to arrange two or more (e.g. a corresponding number of) sample collection devices next to each other into which the liquid can be dispensed simultaneously from the respective sampling devices. In particular, the number of sample collection devices may be such that they at least correspond to the number of eggs in the rack, and preferably the sample collection devices may also be arranged in the same way as the eggs in the rack, e.g. in the form of a grid.

The more sample collection devices are combined into one unit, the easier it is to move this unit relative to the sample collection device to collect the extracted samples.

According to a further aspect, the at least two sample collection devices combined in the unit can be configured by a nonwoven or a titer plate. The method of determining a property of an amount of liquid is used in particular, for example, to determine whether an embryonic structure in an egg will later become a male or female chick by means of the oestrone sulfate concentration of the allantoic liquid. Such a method is a biochemical method which is carried out using a double anti-body technique. On the nonwoven or the titer plate, for example, there are bound oestrone sulfate-specific antibodies. The reaction to determine the concentration of oestrone sulfate, for example, is carried out directly on the sample collection device, i.e. the concentration can be carried out indirectly at the corresponding location of the nonwoven where the sample taken is applied or at the corresponding location of the titer plate or so-called well plate. For further details, reference is made to the German patent application no. DE 10 2015 226 490.4, the disclosure of which is used to determine the oestrone sulfate concentration in allantoic liquid by means of the double antibody technique. In particular, a titer plate coated by direct coating or such a nonwoven can be used as a sampling device. For the determination of the concentration of oestrone sulfate, reference is made to the aforementioned application.

According to a further aspect of the invention, the sampling device may be positioned in a delivery position after sampling and extraction of the same from the respective egg, and the sample collection device, when the sampling device is positioned in the delivery position, may be movable from a sample collection device rest position to a collection position in which the sample may be delivered from the sampling device to the sample collection device.

An actuator, for example, which is controlled by the control device in such a way that after sampling by means of the sampling device and taking it out of the respective egg when the sampling device is positioned in a sampling position, the sample collection device is moved from a sample collection device rest position to a collection position in which the sample is delivered from the sample device to the sample collection device, is associated with the sample delivery device. Thus, the control unit can bring the sample collection device to the sampling device via an actuator in such a way that it does not have to be translationally moved for sample delivery to the sample collection device with the exception of movement in the height direction.

It is therefore possible to configure the sampling device in such a way that, for example, it can only be moved in two directions, namely in the vertical direction and in the lateral direction, thus, in the direction in which the eggs are arranged next to each other in the rack transversely to the oblique orientation of the rack. Nevertheless, there are also variants in which it is preferred to configure the sampling device in such a way that it can be moved translationally in all directions and/or can also be rotated. The sampling device is therefore preferably always moved to a position below the sampling device, especially below the end of the cannula from which the sampled liquid is to be dispensed.

In addition to vertical movement, the sample collection device can also move not only in a horizontal direction but also in another horizontal direction where the eggs lie next to each other.

According to a further aspect of the invention, a rinsing device may be provided which, after sample delivery into the sample collection device, can be moved from a rinsing device rest position to a rinsing position in which the sampling device is rinsed by means of a pressure profile of the pressure generated in the vacuum generating device. After the liquid sample has been discharged from the sampling device, it is rinsed by means of the rinsing device. For this purpose, the sample collection device can first be returned to the sample collection device rest position and the rinsing device can be moved from the rinsing device rest position to the rinsing position. Both situations can take place simultaneously, e.g. using the cannula revolver described above.

The rinsing device is therefore preferably always moved to a position below the sampling device, especially below the end of the cannula, and the sampling device or cannula is immersed in the rinsing device filled with rinsing liquid. The pressure curve in the vacuum hose is controlled via the control device in such a way that rinsing liquid is sucked in and subsequently discharged again. This rinsing device preferably contains alcohol, which denatures the biological material from the egg which remains in the sampling device. Additional rinsing after rinsing with alcohol may, for example, take place via the pneumatic system by pumping demineralized water through the vacuum hoses.

After rinsing, air can also be blown through the sampling device via the pneumatic system in order to dry said device.

After rinsing and drying, the sampling device can be reused to take another liquid sample from the egg.

In particular, the procedure carried out in the egg inspection device is controlled by the control unit in such a way that, insofar as only one sampling device is provided, it takes a liquid sample from the individual eggs according to the grid method and delivers it to a corresponding sample collection device. After each sampling and delivery, a rinsing process is carried out. If several sampling devices are provided next to each other, a corresponding liquid sample can always be taken simultaneously, e.g. from two, three, four, five or ten eggs. This liquid sample is then transferred to a corresponding number of sample collection devices. All sampling devices are then rinsed. The rinsing device may be a simple liquid vessel into which all sampling devices are immersed simultaneously.

According to a further aspect of the invention, the sample collection device and rinsing device for rinsing the sampling device may be configured in one unit. If the sample collection device and the rinsing device are configured as one unit, they can be easily replaced.

According to a further aspect of the invention, the lifting-out device can have an egg stamp which can be moved through a mesh of the rack in order to lift the egg stored in this mesh out of it. In addition, a stop element may be provided, preferably with a cranial egg head stop, against which the egg can be pressed by the egg stamp and which determines the sampling position. The egg stamp can have or be made of a buffering and/or balancing material which allows the egg to be adjusted in the correct direction. An egg stamp preferably moves perpendicularly to the inclined orientation of the rack through a respective mesh of the rack to lift the respective egg out of the rack. During the egg being pushed out of the rack by the egg stamp, the egg stamp is lifted and the egg base is pressed against a stop element to fix the egg. The stop element may be configured to have a curvature corresponding to the curvature of the egg base to hold the egg between the stamp and the stop element so that the axis of rotation of the egg passes through the egg stamp and the stop element. Preferably, the control unit controls the egg stamp and the stop element.

According to a further aspect of the invention, at least one actuator can be assigned to the egg stamp and the stop element which can be controlled via the control unit. The respective actuator of the egg stamp or the stop element causes a translational movement of the egg stamp and the stop element by instruction of the control unit so that these elements are moved translationally perpendicular to the inclined rack. This facilitates pushing the egg through the rack. Since both parts, namely the stamp and the stop element, are equipped with an actuator, these two elements can interact in such a way that they grip and hold the egg between them. In this way, the egg held in the sampling position can be safely sampled.

According to a preferred further aspect of the invention, a position determining device may be provided by which the position of the egg is determined, wherein the control unit controls the positioning of the egg based on the data of the position determining device. The lighting units described below which are preferably provided in the egg stamp, can serve as such a position determining device. As an alternative or in addition, any other method or system, such as a camera system or an infrared system, may also be provided to determine the relative position of the egg and/or in particular the position of internal compartments of the egg, in particular the allantois.

On the basis of the data from the position determining device, the control device can give instructions to position the egg accordingly. The positioning is carried out, for example, by means of the lifting-out device (mechanically and/or by air stream).

According to a further aspect of the invention, a lighting unit can be provided to illuminate the egg in order to determine the position of the egg. Said lighting unit can preferably be configured of one or more LED lamps. Said lighting unit illuminates the egg, which is referred to as the so-called shearing. This allows the positioning of the embryonic chick or the allantois to be better determined. In addition to a single lighting unit, several lighting units can also be provided.

In connection with this further aspect, it may be advantageous that the egg stamp works together with another rotating element that rotates the egg in such a way that a predetermined position of the egg can be better reached. In this case, the system can be buffered.

The egg stamp can be provided with the lighting unit in accordance with a further aspect of the invention. Advantageously, the lighting unit can be arranged inside the egg stamp.

According to a further aspect of the invention, a UV lamp unit can be provided which illuminates at least one of the following devices to kill bacteria and/or germs: eggs, sampling device, rinsing device, sample collection device, lifting-out device. In particular, it is advantageous to arrange the UV lamp unit as a kind of UV tube above the inclined rack and between the sampling device and the sample collection device. The UV tube is preferably arranged transversely to the inclined position of the rack.

According to a preferred further aspect of the invention, the control unit may be configured in such a way that a sampling of the eggs in the racks is automated after the racks with the eggs have been introduced into the egg inspection device, and after all eggs of the rack have been sampled, a corresponding information is output. This means that a kind of program is stored in the control device in which an automated method for sampling the eggs is carried out.

Insofar as the invention is based on the lifting-out device, this can also be omitted completely and any combination or configuration of sampling device, rinsing device, sample collection device, rack, control device, position determining device, or even an individual of these elements can form an invention in itself. The aforementioned devices or elements can also each form their own invention independently of the other components of the overall device.

BRIEF DESCRIPTION OF THE FIGURES

Further preferred further aspects of the invention result from the following described embodiment in connection with the drawing.

Therein:

FIG. 6 shows a detail view of an egg stamp of the embodiment of FIG. 2.

DETAILED DESCRIPTION

Figure 1:
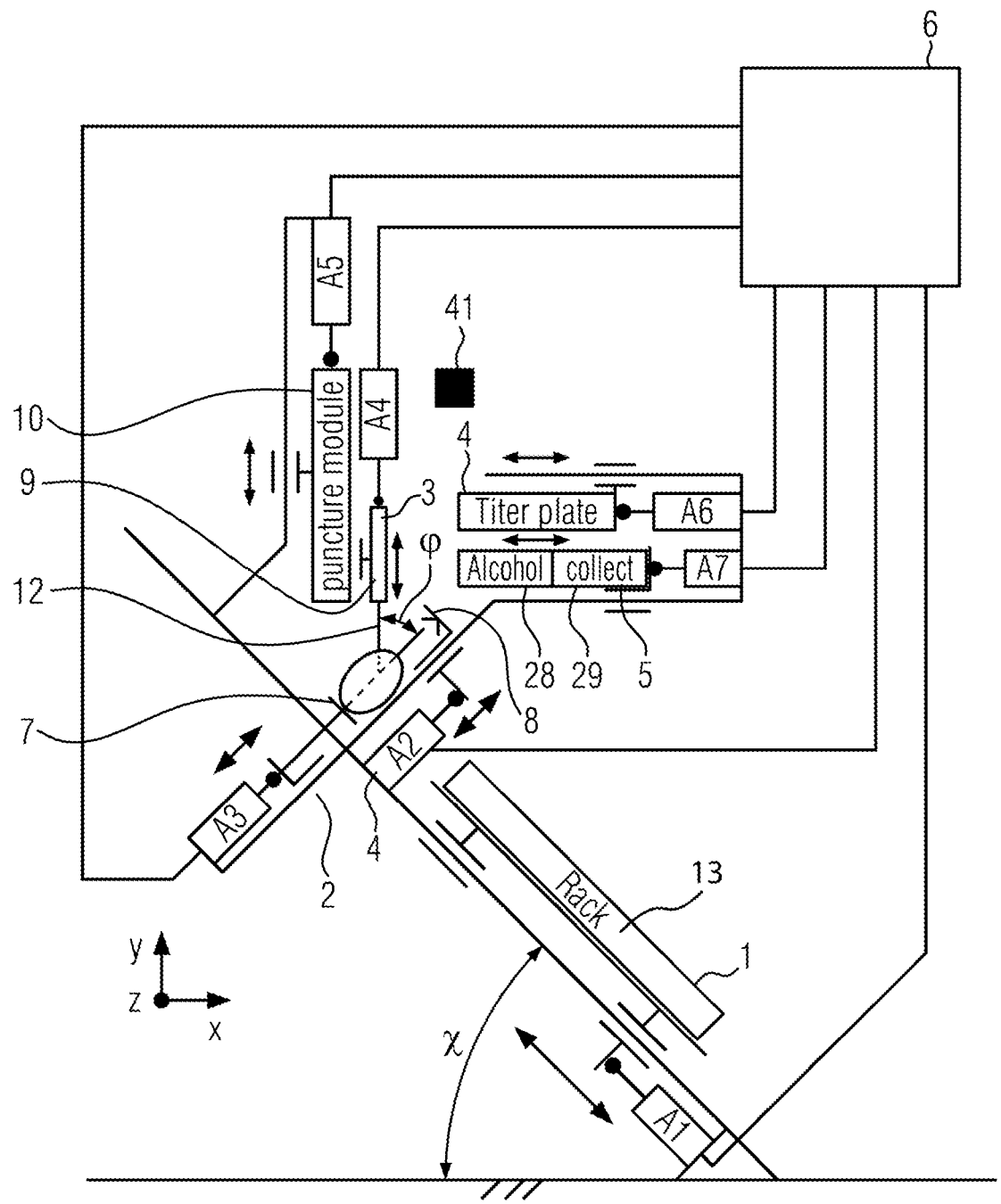
FIG. 1 shows a schematic cross-sectional view of an embodiment of an egg inspection device.

FIG. 1 shows a schematic cross-sectional view of an embodiment of an egg inspection device.

The egg inspection device includes a feeding device 1, a lifting-out device 2, a sampling device 3, a sample collection device 4, a rinsing device 5, and a control unit 6. The lifting-out device 2 includes an egg stamp 7 and a stop element 8. The control unit 6 controls, according to actuators A1, A2, A3, A4, A5, A6, A7, in order to position or move the aforementioned elements or units.

Alternatively to the fact that the lifting-out device is a mechanical lifting-out device with the egg stamp 7 as well as the stop element 8, a lifting-out device operated by means of an air stream can also be provided in which the egg is lifted by means of an air stream. In this way, the egg can be lifted out by means of an air stream and pressed against a stop element in order to be brought into the correct position. In this case, a hose with an opening below the egg is positioned in the rack and compressed air is used to lift the egg in the air stream.

In order to enable the positioning and alignment of the egg to be sampled, a guided lifting of the egg is advantageous. This can be done via the egg stamp, preferably via rotatably mounted egg stamps, and/or via an air stream. The egg is then held in position from the other side, e.g. with a soft suction cup. This fixation can also be done mechanically and/or by air stream. In addition, the egg position can be guided ventrally.

The feeding device 1 comprises a first actuator A1, the lifting-out device 2 from the egg stamp 7 and the stop element 8, a second actuator A2 which sets the stop element 8, and a third actuator A3 which sets the egg stamp 7. The syringe 9 shown in this Figure is drawn over a fourth actuator A4 shown in FIG. 1. A base plate 10 with the attached syringe 9 forms a sampling unit, whereby the syringe 9 forms the sampling device. The sampling unit as a whole is placed over a fifth actuator A5. A sixth actuator A6 is assigned to the sample collection device 4 and a seventh actuator is assigned to the rinsing device 5.

Figure 2A:
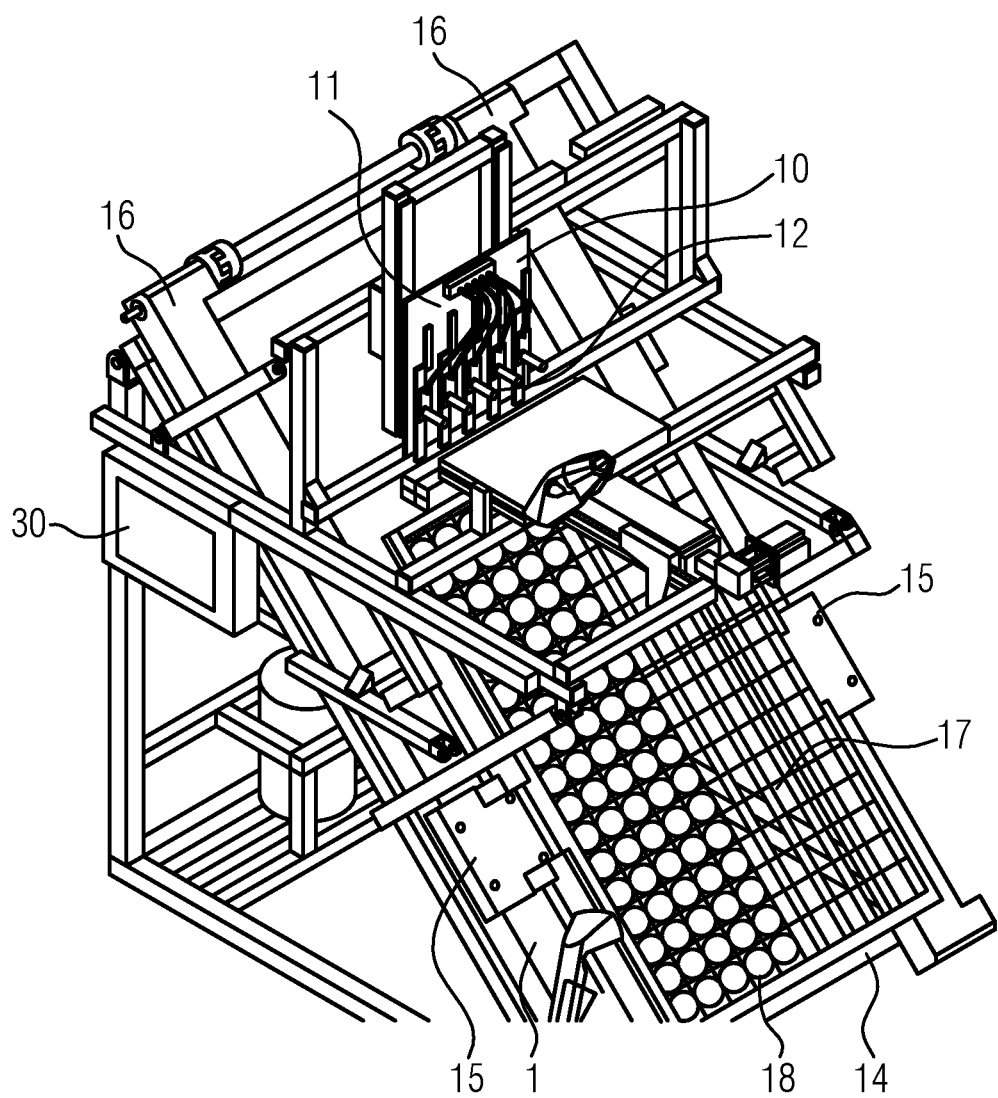
FIG. 2A shows a top view on an egg inspection device which is similar to that of FIG. 1, wherein the rack is positioned in a starting position.

FIG. 2A shows a top view of the egg inspection device shown in FIG. 1, wherein a rack 13 is shown positioned in a starting position. A difference between the egg inspection device shown in FIG. 2 and the first embodiment shown in FIG. 1 is that no simple syringe is provided on the sampling unit as sampling device 9, but sampling takes place via cannulas 12 connected to vacuum hoses 11, each cannula with vacuum hose 11 connected thereto forming a sampling unit 9, and thus five sampling devices are provided in the sampling unit. Any number of sampling units, in particular 5, 10, 15, sampling devices 9, can be combined into one unit between one and a large number of sampling units.

FIG. 2A shows a starting position after the rack 13 has been inserted into the feeding device 1 as presently, for example, half filled with eggs 18. In the present case, the feeding device 1 is designed as a kind of frame 14 in which the rack 13 can be inserted in such a way that its side walls are essentially flush with the frame 14.

Figure 2B:
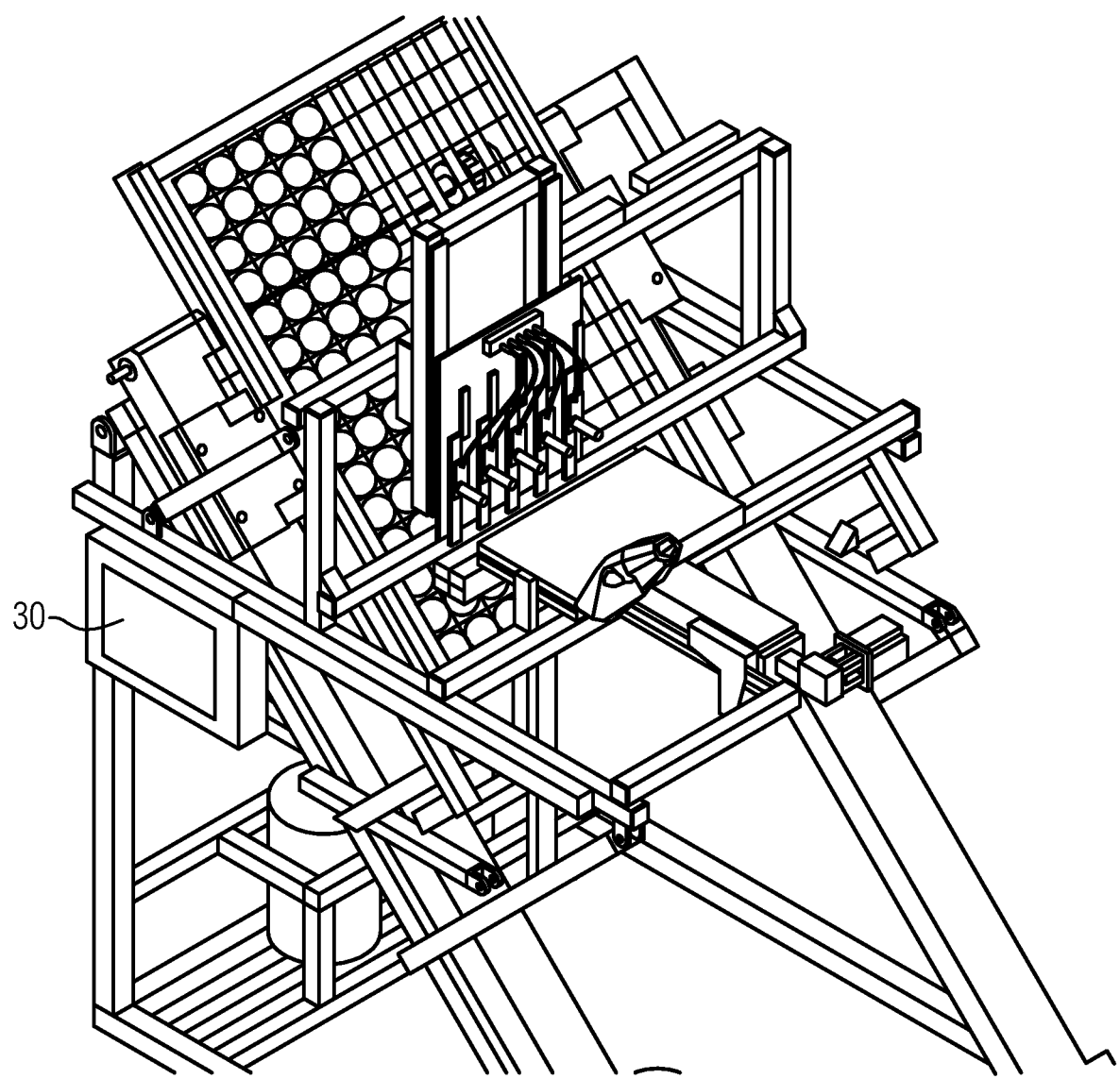
FIG. 2B shows a top view of the egg inspection device of FIG. 2A, wherein the rack is positioned in an end position after having sampled all eggs.

Said frame has a carriage 15 on two sides opposite each other in the transverse direction of the device, which carriage is movably mounted on corresponding rails 16 and can thus be moved from the starting position shown in FIG. 2A to an end position shown in FIG. 2B via the control unit 6 by means of the first actuator A1 not shown in FIG. 2A.

In order to subsequently facilitate the identification of the individual directions, the direction of gravity, i.e. the direction in FIGS. 1, 2A and 2B is to be referred to from top to bottom as the y-axis, the axis perpendicular to this vertical, i.e. to the y-axis and transverse to the rack 13 as the z-axis, and the axis in which the inclination of the rack 13 extends is to be referred to as the x-axis. A corresponding coordinate system is shown in FIG. 2A. A corresponding coordinate system is also shown in FIG. 1. The first actuator A1 ensures a translational movement of the feeding device 1 in the y-x plane. The second actuator A2 and the third actuator A3, ensure a translational movement of the individual elements of the lifting-out device within the y-x plane and perpendicular to the movement of the first actuator A1. The fourth or fifth actuator A4, A5 ensures a translational movement of the corresponding elements (sampling device or sampling unit) in the y-direction. The seventh or eighth actuator A7, A8 ensures a translational movement of the corresponding elements in the x-direction.

The rack 13 is configured as a kind of grid 17 with equally large meshes, wherein one single egg 18 can be held in each mesh. Since the meshes are limited only by strip-like walls standing upright, each egg 18 lies with its tip downwards in the respective mesh. That is, FIG. 2A shows a base side of the eggs 18. The eggs 18 lie in a matrix, wherein in the present example five eggs 18 lie in transverse direction (z-axis) next to each other and 17 eggs in longitudinal direction or diagonal direction (x-axis) behind each other. In the following, the direction of the z-axis is always referred to as next to each other for the eggs and the direction of translation (x-axis) of the feeding device 1 is always referred to behind each other for the eggs.

Figure 4A:
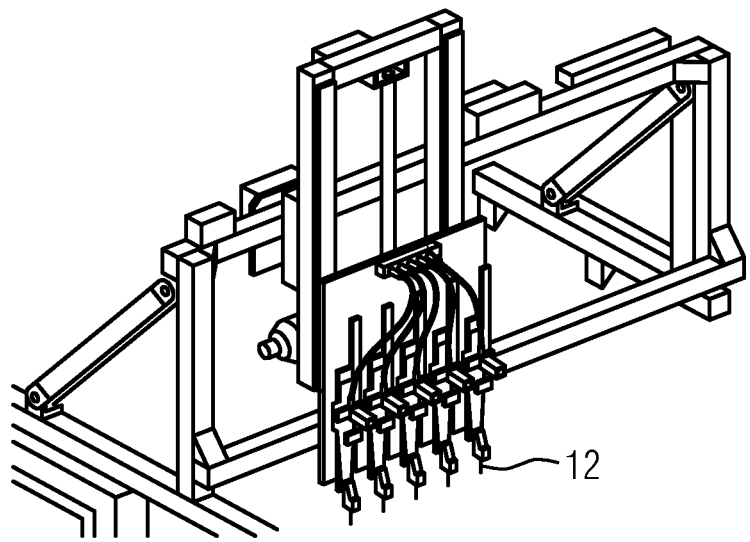
FIG. 4A shows a section of the egg inspection device of FIG. 2 in which a sampling device with sampling units is shown.
Figure 4B:
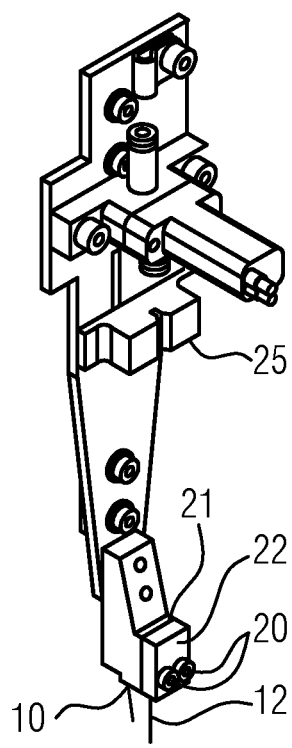
FIG. 4B and FIG. 4C shows an individual sampling device of the sampling unit of FIG. 4.
Figure 4C:
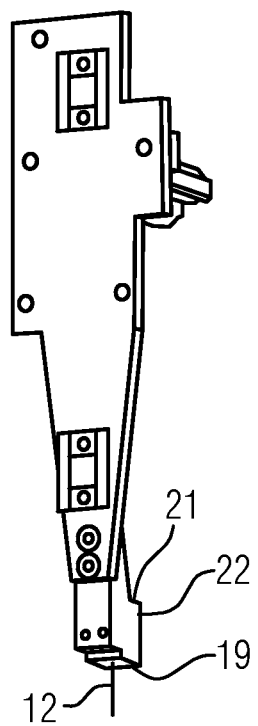

In the present embodiment, five sampling devices 3 are provided on the base plate 10 to form the sampling unit. Each of the sampling devices 3 has a modular structure and is described in more detail below in relation to FIGS. 4A to 4C. As shown in FIGS. 4B and C, each sampling device 3 is configured as a module which, for example, can be attached to the base plate 10 via screw connections. A contact surface 19, from which the cannula 12 protrudes, is provided on a side of the module which is directed towards the egg when mounted on the base plate 10 (hereinafter referred to as the bottom side of the module). The cannula 12 is held by a kind of clamp connection between the plate elements 21, 22 of the module by pressing the plate element 22 together by means of the two fastening elements 20 shown in FIG. 4B, which in this case are hexagon socket screws. As shown in FIG. 4A, a vacuum hose 11 is connected to the rear of each cannula 12, which is preferably a thin metal cannula with a sharp tip. The vacuum hoses 11 are connected to a pneumatic system which is not shown in detail in the Figures. With the negative pressure generated in the pneumatic system, a predetermined quantity of liquid can be taken from the egg 18 with the cannula 12 after the respective egg has been inserted.

The sampling procedure is described in more detail below in conjunction with FIG. 3.

Figure 3:
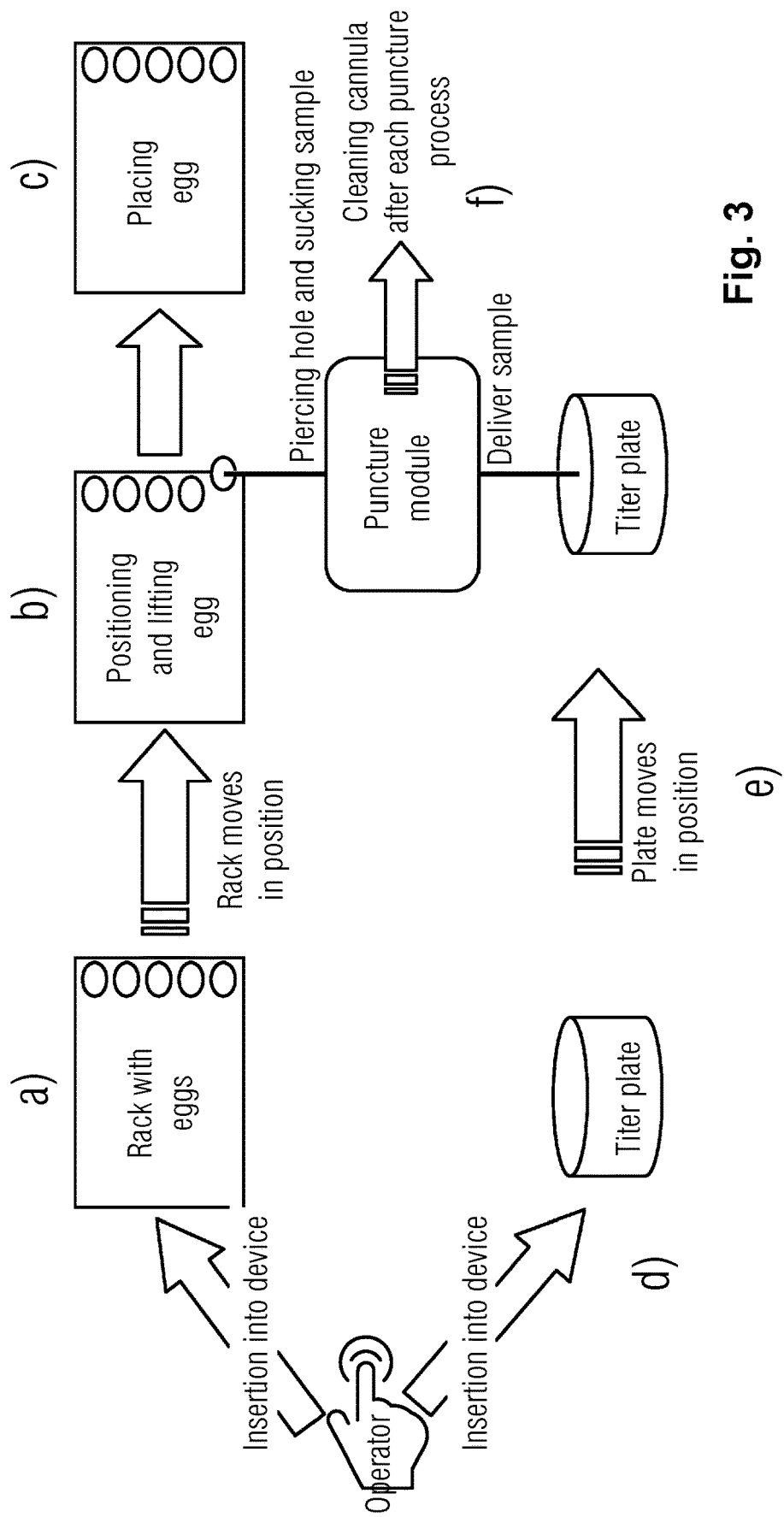
FIG. 3 shows a schematic diagram of the method for sampling an egg as is carried out in the egg inspection devices of FIG. 1 or 2.

After an operator has inserted the rack 13 loaded with the eggs 18 into the feeding device 1 (step a) in FIG. 3), the egg 18 is positioned. For this purpose, the feeding device 1 is moved via the control unit 6 in such a way that the first row of eggs, seen in the translation direction of the rack (x-axis), stops at the level of the sampling device 3 (see FIG. 2A) (step b) in FIG. 3). In this position, for example, five eggs are arranged below the respective 5 sampling devices 3 of the sampling unit. With the egg stamps 7 shown in FIG. 6, the five eggs are simultaneously pressed out through the meshes of the rack 13 substantially perpendicular to the rack 13, that is, perpendicular to the surface formed by the frame 14 of the rack 13 or perpendicular to the inclined feeding plane, in order to be lifted out of the rack 13 and pressed against the stop element 8 schematically shown in FIG. 1.

The eggs with their thicker rear side are lifted out of the rack at an oblique angle between 20 and 80°. The angle φ (see FIG. 1) between the rotation axis (longitudinal direction) of the egg 18 and the vertical direction (y-axis), i.e. the direction in which the cannula 12 is pierced into the egg 18 (in the present case the direction in which the sampling unit can be moved in its vertical direction), corresponds due to trigonometry to the angle χ, at which the feeding device 1 feeds the rack 13 obliquely (see FIG. 1). The angle φ between the rotation axis (longitudinal direction) of the egg 18 and the cannula 12 corresponds to the angle χ between the x-axis (in the present case the bottom surface) and the translation direction of the feeding device 1, since its legs are perpendicular to each other in pairs. The lifting direction of the eggs is perpendicular to the rack plane, which corresponds to the translational plane.

After lifting out the egg 18, this is now held between the egg stamp 7 and the stop element 8.

In the present example, the complete base plate 10 with the sampling devices 3 attached to it that is the sampling unit is then lowered on the y-axis so that the five cannulas 12 simultaneously pierce the five eggs 18 lifted up next to each other.

As soon as the contact surface 19 of the respective sampling unit 3 hits the shell of the respective egg 18, this is detected by the control unit 6 and the sampling is started.

For this purpose, after the hole in the egg 18 has been created by piercing with the respective cannula 12, a vacuum is created in the vacuum hoses 11 so that a corresponding amount of liquid is sucked out of the egg.

The predetermined target quantity of the liquid extracted from the egg is detected by a light barrier 25 shown schematically in FIG. 4B. This means that as soon as the liquid meniscus in the vacuum hose 11 reaches the light barrier 25, the pressure is kept constant.

The sampling unit is then retracted again (in vertical direction; y-axis) and the cannulas 12 are pulled out of the eggs. The tips of the cannulas 12 should preferably be held at such a height that the sample collection device 4 or the rinsing device 5 can be moved translationally below the tip of the cannula by means of the sixth or seventh actuator A6, A7 shown in FIG. 1, as indicated by the arrows in FIG. 1, out of the sample delivery and cleaning assembly provided with reference sign 26.

In the present example, this is a so-called titer plate in which individual sample collection devices 4, i.e. for example cavities, are arranged side by side and one behind the other, resulting in a matrix of sample collection devices 4.

After translational movement of the titer plate (in x-axis) under the cannula ends (step e) in FIG. 3), the corresponding pressure is now applied to the vacuum hoses 11 by means of the control unit 6 so that the amount of liquid extracted from the eggs 18 is discharged from the sampling devices 3 into the corresponding sample collection device 27 provided below. This is done essentially simultaneously so that after five amounts of liquid have been taken from five eggs 18 at the same time in the present example, also from five liquid samples, one of each is delivered to the corresponding sample collection device. The corresponding titer plate (step d) in FIG. 3) is inserted into the egg inspection device beforehand by the operator, as is the rack with the eggs.

An analysis is then carried out in each of the sample collection devices 3 and in the present case, for example, the concentration of oestrone sulfate in the allantoic liquid taken from the eggs 18 is determined in order to conclude the sex of the embryonic chicks. Such a method for the biological determination of the oestrone sulfate concentration for the identification of female and male chicken embryos is described in the German patent application number 10 2015 226 490.4, the disclosure of which is included in this respect by this reference. The concentration of oestrone sulfate can be indirectly determined by means of a colorimetric measurement.

After the individual amounts of liquid removed from the eggs have been transferred to the sample collection devices 4, the five eggs 18 held by the lifting-out device are returned to the position of the rack (step c) in FIG. 3). Alternatively, this can be done immediately after liquid extraction and before sample delivery.

The titer plate, i.e. the matrix of sample collection devices 4, is moved back to the basic position shown in FIG. 2B or 1 in the sample delivery and cleaning group.

Figure 7:
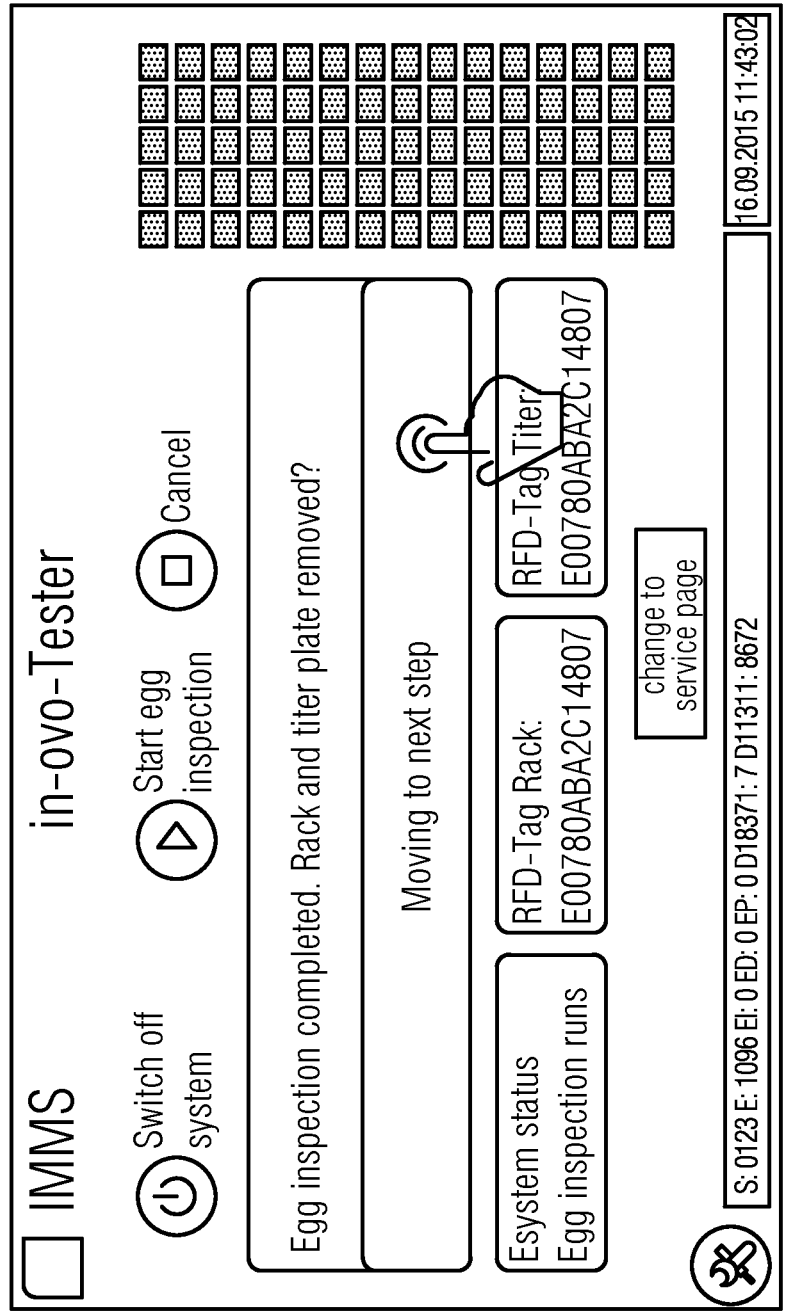
FIG. 7 shows an example of a user interface of the software by means of which the device is controlled.

For cleaning the cannulas 12, the rinsing device 5 which in the present example consists of a trough 28 filled with alcohol and a collecting vessel 29, is now moved by means of the seventh actuator A7 (see FIG. 1), as shown in FIG. 7, from the basic position within the sample delivery and cleaning group into a rinsing position not shown in the Figure, in which the rinsing device 7 comes to a standstill substantially below the cannulas 12, i.e. below the respective sampling device 3. The cannulas can be cleaned after each piercing operation (step f) in FIG. 3).

In a first step, the sampling unit is moved downwards in the vertical direction, i.e. on the y-axis, in order to immerse the cannulas 12 with their tips in the trough 28 filled with alcohol.

Via the control unit 6, a small amount of alcohol is now sucked from the trough 28 into the cannula in order to denature the biological residues. After this, the sampling unit is retracted upwards in the vertical direction (along the y-axis) via the fifth actuator A5 and the collecting vessel 29 is moved from the rinsing position to a rinsing solution discharge position so that the collecting vessel 29 is arranged below the sampling device 3. After this, demineralized water which is stored in a container of the device not shown in the Figures is introduced into the cannulas 12 via the vacuum hoses and the cannulas 12 are rinsed with this water which is collected in the collecting vessel 29.

After rinsing, drying of the cannulas and/or vacuum hoses preferably takes place. This can be done, for example, by means of separate air nozzles which are provided in the inspection device and blow the cannulas 12 from the outside. In the present example, air is blown through the vacuum hoses 11 and thus the cannulas 12 are blown by means of the pneumatic system.

After the sampling devices have been cleaned, the rinsing device 5 is pulled back into the basic position as shown in FIG. 1.

Subsequently, the feeding device 1 is positioned via the control unit 6 in such a way that the rack 13 is shifted obliquely forward one row in the direction of translation in order to sample the next row of five eggs 18 simultaneously.

This prescribed method shall be repeated until all consecutive eggs of the rack have been sampled in the longitudinal direction.

The position in the matrix of sample collection devices 4 in which the amount of liquid extracted is placed on the titer plate corresponds to the position of the eggs in the racks. In this way, each egg in the rack can be clearly assigned to a single sample collection device.

The entire egg inspection device may be operated via a touch-sensitive computer screen connected to the control unit 6. The computer screen in FIGS. 2A and B is provided with reference sign 30.

An example of a software user interface that controls the device displayed on the computer screen 30 is shown in FIG. 7. FIG. 7 shows a state of the user interface in which the sampling method was completed once. Therefore, in the schematic arrangement of the eggs in the racks shown on the right side, the squares are shown filled out.

If a particular egg has not yet been sampled, these squares are not filled out, but merely drawn by a circumferential line.

In addition, FIG. 7 shows that each rack and the corresponding titer plate, into which the samples are delivered, can be clearly assigned to each other. In the present example, this is ensured by an RFID tag, which is provided on a rack and on the titer plate. A tray number stored in the RFID tag can be assigned to a titer plate number.

Once all eggs of the rack have been sampled as desired, characterization is usually not performed within the device according to the invention but in a separate device. This means that the titer plates filled with samples are removed from the device and fed to an appropriate device to determine the oestrone sulfate concentration. The fact that the arrangement of the eggs in racks is known and the position in which the corresponding liquid is discharged from an egg in the racks means that it is possible to determine later which egg in the racks corresponds to which result on the titer plate.

Since the egg size can vary depending on the age of the laying hen, it is often difficult to sample all eggs with the same cannula length (projection of the cannula from the contact surface 19). This is because the protruding cannula length determines the depth from which the corresponding amount of liquid is taken from egg 18. For example, to extract allantoic liquid, a predetermined depth must always be reached at a previously described angle.

The protruding length of the cannula can be adjusted by means of the control unit. For example, the control unit can set and vary the length of the cannula depending on the information about the respective egg, and thus selectively set a depth for each corresponding egg depending on its characteristics, e.g. its thickness, from which the amount of liquid is taken.

Alternatively or additionally, or also if the protruding cannula length cannot be changed, the control unit can move the sampling device forward until the cannula is immersed in the liquid in the egg (allantois). The control unit can, for example, detect the cannula being immersed in a liquid (allantois) and stop the forward movement of the sampling unit when the desired depth is reached. The suction process is then started, for example.

The length adjustment of the cannulas can also be an invention in itself, independent of the egg inspection device.

Figure 5A:
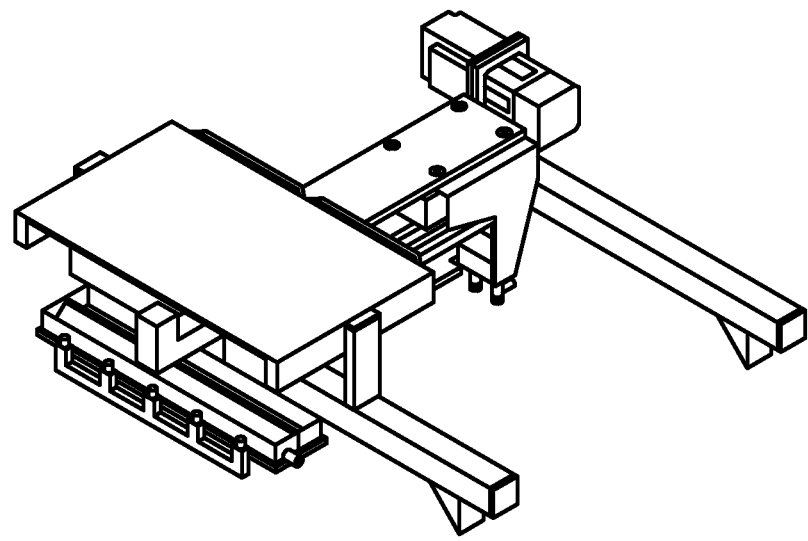
FIG. 5A shows a unit consisting of delivery unit and rinsing unit.
Figure 5B:
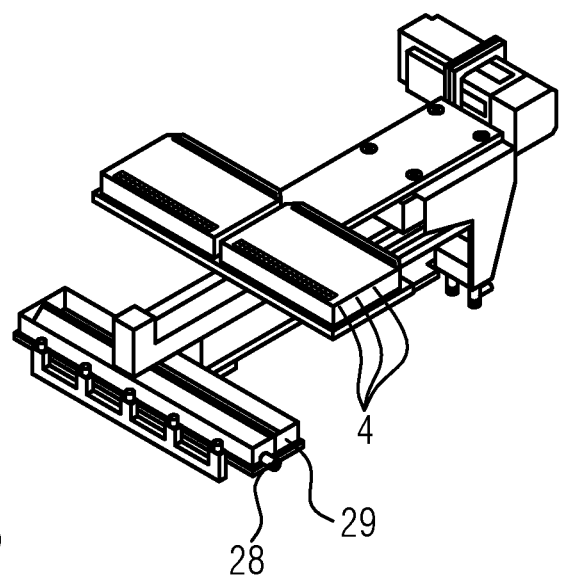
FIG. 5B shows the unit of FIG. 5A, wherein a protective covering is removed.

FIGS. 5A and 5B show a detailed view of the sample delivery and cleaning assembly 26. This has a cover 35 for protection against environmental influences such as dust, a first storage surface 36 on which the rinsing device 5 rests, and a second storage surface 37 on which the sample collection devices 4 combined in the titer plate are placed. As shown in FIG. 5B, two titer plates are provided. Instead of the titer plate, a nonwoven can also be provided in which the extracted sample is discharged at various points.

Each of the two storage surfaces is fixed separately to a translationally movable arm. The two arms can be moved independently of each other via the seventh actuator A7, the rinsing device 5 or the titer plate/nonwoven from the basic position to the corresponding delivery position for the sample unit or for rinsing or blowing out position for the rinsing unit.

The cleaning assembly 26 can also be an invention in itself independently of the egg inspection device.

As shown in FIG. 6, the egg stamps 24 are designed as slightly conical plastic sleeves 39 which have in their center an element 38 of regulating and balancing material, e.g. compressible material. The egg stamps 24 are moved translationally by the third actuator A3 shown in FIG. 1 via the pistons attached to them on the bottom side. Here, the tip of the eggs is brought into contact with the element 38 of regulating and balancing material and the eggs are held by the conical plastic sleeves 39 which are designed as egg heads and which are supported on their circumferential direction by suction cups.

In order to better determine the position of the eggs, instead of the element 38 made of regulating and balancing material, lighting elements such as an LED unit can also be used to perform so-called shearing. By means of this illumination of the eggs, positions of different groups within the egg can be better determined. For example, the egg can be readjusted in order to better hit the allantois during piercing. In addition, it is conceivable that instead of the cannulas 12 which are mechanically height-adjustable by means of the fastening elements, further actuators are provided on the sampling devices 3 which enable automatic adjustment of the cannula length via the control device 6.

It is advantageous, for example, to determine the size and shape of each egg 18 by means of an observation device, such as a camera, in order to obtain information about the characteristics or position of each egg by means of image processing methods. This information can be passed on to the control unit 6 which then adjusts the length accordingly via the actuators of the sampling devices for the respective cannula 12 of the respective sampling device 3. A connection with camera and light source for the alignment of the egg is conceivable.

In the present embodiment, five eggs are sampled at the same time. Sampling is not limited to five eggs. A single sampling unit is sufficient for this invention. Preferably, however, at least two eggs, in particular up to ten eggs, can be sampled simultaneously.

Even if in the second embodiment a vacuum control of the sampling is carried out, alternatively, as in the first embodiment, a simple syringe can be provided which can be operated via a mechanical piston.

The present configuration of the egg inspection device makes it particularly effective to puncture the eggs in an automated manner at an oblique angle, preferably by puncturing the sampling device, i.e. the cannula attached to it, in a vertical direction, i.e. in the direction of gravity, each egg being individually aligned slightly obliquely at an angle of 20° to 80°.

For this purpose, the eggs stored in the racks are fed obliquely to the direction of gravity together with the racks via the feeding device and then lifted out of the respective mesh of the racks by means of the lifting-out device perpendicular to this oblique surface.

The eggs are held in the lifting-out device, presently by means of plastic sleeves 39 which are formed as suction devices comprising the egg head, and the stop element individually at the side, front and rear and independently of the rack, in order to ensure a selective exact piercing under a predefined angle and to sample eggs.

By piercing the cannula 12 in a vertical direction (gravity direction), the angle at which the feeding device 1 feeds the eggs substantially corresponds to the inclination of the eggs with respect to the cannula 12.

Particularly advantageous angle ranges are between 30° and 60°, preferably between 40° and 50°, in particular 45°. In particular, it is advantageous to define the angle in such a way that the angle between the cannula and the axis of rotation of the egg is seen from the base of the egg and not from the tip.

If the egg is twisted by exactly the angle described above in relation to its base, it has been shown that the allantoic liquid accumulates to a suitable extent at a well-defined position in the egg so that a well-defined amount of allantoic liquid can be extracted through the cannula.

In order to make this procedure even more reproducible, it is advantageous that the tip of the cannula used has at least two openings. It has been shown that if only one opening is used, an ideal sample cannot be taken under all conditions. More than two openings in the cannula are also possible. In some circumstances, a single opening in the cannula may also be advantageous.

It is advantageous to provide a UV lamp unit 41 (see FIG. 1) for the inspection device so that UV light is emitted from this UV lamp unit 41 to the region where the eggs are sampled.

In particular, a UV tube can be used which extends along the z-axis, i.e. along the direction of the eggs lying next to each other. In particular, it has been shown that placing the UV lamp unit 41 between the sampling device 3 and the sample delivery and cleaning assembly 26 is advantageous.

In addition, the inclination with which the feeding device 1 feeds the rack can also be changed selectively depending on egg characteristics. The settings of the entire device can be made via the control unit 6.

In particular, insofar as the egg inspection device is equipped with a system for determining the position of the eggs, for example an optical camera system, this image information can be processed in order to selectively determine the position of the individual eggs for extracting the amount of liquid and/or the length of the cannula as a function of the egg thickness, the egg size and/or the amount of liquid to be extracted.

The vacuum hoses can be configured such that their pressure can be variably adjusted independently of each other for selective removal of liquid amounts adapted to the egg condition.

In addition, instead of the individual sampling devices being attached to a base plate, it may also be advantageous that the individual sampling devices can be moved relative to each other.

Insofar as the invention is based on the lifting-out device, this can also be omitted completely and any combination or design of sampling device, rinsing device, sample collection device, rack, control device, position determining device, or even a single one of these elements can form an invention in itself. The aforementioned devices or elements can also each form their own invention independently of the other components of the overall device.

The disclosure of the German patent application no. 10 2015 226 490.4 on the method and details for determining the oestrone sulfate concentration in allantoic liquid by means of the double antibody technique is made part of the disclosure of the present application by means of this reference.

LIST OF REFERENCE NUMBERS

Feeding device 1
Lifting-out device 2
Sampling device 3
Sample collection device 4
Rinsing device 5
Control unit 6
Egg stamp 7
Stop element 8
Syringe 9
Base plate 10
Vacuum hose 11
Cannula 12
Rack 13
Frame 14
Rail 16
Grid 17
Egg 18
Contact surface 19
Cannula 12
Fastening element 20
Plate element 21, 22
Light barrier 25
Sample delivery and cleaning assembly 26
Trough for alcohol 28
Collecting vessel 29
Computer screen 30
Gauge 31
Step 32
Counter surface 33
Cover 35
First storage surface 36
Second storage surface 37
Element of regulating and balancing 38
Conical plastic sleeve 39
UV lamp unit 41
First actuator A1
Second actuator A2
Third actuator A3
Fourth actuator A4
Fifth actuator A5
Sixth actuator A6
Seventh actuator A7

The invention claimed is:
1. An egg inspection device comprising:
a rack loaded with eggs;
a feeding device; and
a means by which a hole is generated in the respective eggs which are loaded in the rack,
wherein the feeding device is configured such that it feeds the rack at an oblique angle of between 20° and 80° to a plane perpendicular to a direction of gravity to the means by which a hole is generated in an egg, through which an amount of liquid to be taken can be extracted from the egg, and
wherein the hole in the egg is formed at such a position that an angle between an axis of rotation of a respective egg and the direction of the means by which a hole is generated in the respective egg is between 30° and 60°.

2. The egg inspection device according to claim 1, wherein the means by which a hole is generated in the respective egg is a sampling device by means of which the liquid sample to be taken can be extracted from the respective egg of the rack loaded with eggs.

3. The egg inspection device according to claim 2, wherein the device comprises a control unit by means of which the feeding device and the sampling device can be controlled.

4. The egg inspection device according to claim 3, wherein the sampling device has a cannula which is connected to a vacuum generating device, wherein the amount of liquid to be extracted from the respective egg can be controlled by means of the control unit via a pressure generated in the vacuum generating device.

5. The egg inspection device according to claim 2, wherein the sampling device is movable in the direction of gravity and parallel to a surface within which the rack is translationally movable by the feeding device and is movable in the direction transverse to the direction of translation of the rack prescribed by the feeding device.

6. The egg inspection device according to claim 2, wherein a first sample collection device is provided which collects the amount of liquid extracted from the respective egg by the sampling device and discharged from the sampling device.

7. The egg inspection device according to claim 6, wherein at least two sample collection devices are provided which are combined in one unit and from which the amount of liquid extracted from the respective egg by at least two sampling devices can be delivered.

8. The egg inspection device according to claim 7, wherein the at least two sample collection devices are configured by a nonwoven or a titer plate.

9. The egg inspection device according to claim 3, wherein a position determining device is provided by means of which the position of the respective egg can be determined, wherein the control unit controls a positioning of the respective egg based on data of the position determining device.

10. An egg inspection device comprising:
a rack loaded with eggs; and
a feeding device,
wherein the feeding device is configured such that it feeds the rack at an oblique angle of between 20° and 80° to a plane perpendicular to a direction of gravity to a means by which a hole is generated in an egg, through which an amount of liquid to be taken can be extracted from the egg,
wherein the hole in the egg is formed at such a position that an angle between an axis of rotation of a respective egg and the direction of the means by which a hole is generated in the respective egg is between 30° and 60°,
wherein the means by which a hole is generated in the respective egg is a sampling device by means of which the liquid sample to be taken can be extracted from the respective egg of the rack loaded with eggs, and
wherein the sampling device is movable in the direction of gravity and parallel to a surface within which the rack is translationally movable by the feeding device and is movable in the direction transverse to the direction of translation of the rack prescribed by the feeding device.

11. An egg inspection device comprising:
a rack loaded with eggs; and
a feeding device,
wherein the feeding device is configured such that it feeds the rack at an oblique angle of between 20° and 80° to a plane perpendicular to a direction of gravity to a means by which a hole is generated in an egg, through which an amount of liquid to be taken can be extracted from the egg,
wherein the hole in the egg is formed at such a position that an angle between an axis of rotation of a respective egg and the direction of the means by which a hole is generated in the respective egg is between 30° and 60°,
wherein the means by which a hole is generated in the respective egg is a sampling device by means of which the liquid sample to be taken can be extracted from the respective egg of the rack loaded with eggs,
wherein a first sample collection device is provided which collects the amount of liquid extracted from the respective egg by the sampling device and discharged from the sampling device,
wherein at least two sample collection devices are provided which are combined in one unit and from which the amount of liquid extracted from the respective egg by at least two sampling devices can be delivered, and
wherein the at least two sample collection devices are configured by a nonwoven or a titer plate.

\* \* \* \* \*